United States Patent [19]

Jacquin

[11] 4,312,741

[45] Jan. 26, 1982

[54] PROCESS AND APPARATUS FOR CATALYTIC HYDROCARBON CONVERSION

[75] Inventor: Yves Jacquin, Sevres, France

[73] Assignee: Institut Francais du Petrole, Rueil-Malmaison, France

[21] Appl. No.: 167,281

[22] Filed: Jul. 9, 1980

[30] Foreign Application Priority Data

Jul. 9, 1979 [FR] France ................................ 79 17947

[51] Int. Cl.$^3$ ........................ C10G 1/00; C10G 1/06; C10G 45/00; C10G 35/00
[52] U.S. Cl. ................................ 208/11 LE; 208/10; 208/143; 208/152; 208/213; 208/254 H; 518/706; 208/179
[58] Field of Search ............ 208/10, 143, 152, 11 LE; 260/449 L

[56] References Cited

U.S. PATENT DOCUMENTS

| | | | |
|---|---|---|---|
| 2,762,683 | 9/1956 | Massey | 208/143 |
| 2,921,817 | 1/1960 | Berg | 208/152 X |
| 3,321,393 | 5/1967 | Schuman | 208/10 |
| 3,652,451 | 3/1972 | Boyd | 208/143 X |
| 3,708,420 | 1/1973 | Irvine | 208/156 |
| 3,950,244 | 4/1976 | Chun et al. | 208/143 |
| 4,111,663 | 9/1978 | Wolk et al. | 208/10 |

*Primary Examiner*—Delbert E. Gantz
*Assistant Examiner*—William G. Wright
*Attorney, Agent, or Firm*—Millen & White

[57] ABSTRACT

A catalytic process for the conversion of hydrocarbons or bituminous shales or carbon monoxide in the liquid phase in contact with hydrogen flowing upwardly through a series of successive stages, each containing a catalyst bed either semi-stationary or dispersed in the charge, the catalyst being maintained at each stage by an upward flow of hydrogen or hydrocarbon supplied below an opening in the partition wall between two successive stages and periodically allowed to pass from one stage to the next through said opening, by discontinuing said upward flow.

10 Claims, 4 Drawing Figures

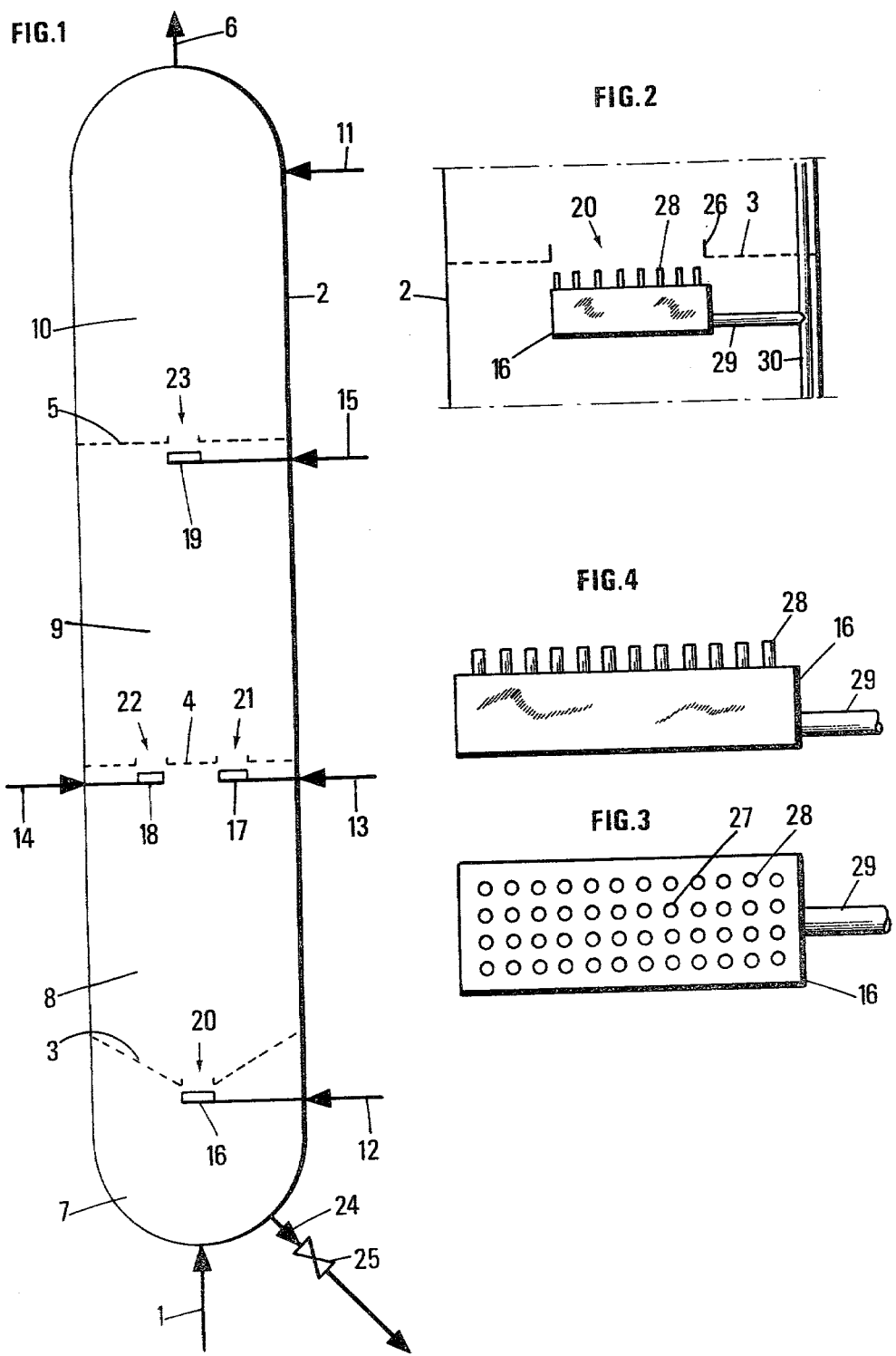

PROCESS AND APPARATUS FOR CATALYTIC HYDROCARBON CONVERSION

BACKGROUND OF THE INVENTION

This invention concerns a liquid phase process and an apparatus for the catalytic conversion of hydrocarbons or carbon monoxide in the presence of hydrogen.

Various processes are known for the hydrotreatment of heavy hydrocarbon charges or of carbon monoxide, in the liquid phase, making use of a dispersed catalyst, and particularly a process wherein the catalyst bed is in dispersed or expanded form, the dispersion or expansion being produced by the upward circulation of the liquid phase and/or hydrogen or a hydrogen-containing gas. An example of such a process is the H-oil process for a hydrocarbon liquid charge. This type of process does not provide for a satisfactory use of the catalyst; as a matter of fact, the catalyst withdrawn from the reactor is a mixture of very substantially deactivated catalyst, of moderately deactivated catalyst and of almost new catalyst and the sorting of the catalyst particles according to their deactivation degree is difficult to achieve.

According to an improvement to said technique (catalyst in a dispersed or expanded form), there is used a series of superposed beds of the same type. The fresh catalyst is introduced at the upper stage of the reactor, preferably after a previous sulfiding, while the stages located below contain a catalyst which is the more deactivated as it is at a lower stage. Periodically the catalyst of one stage n is allowed to go down to the next lower stage n+1, while the less used catalyst of the upper stage n−1 passes to the stage n, and similarly for all the stages. The catalyst of the last stage, at the bottom of the reactor, is discharged, while the fresh catalyst is introduced to the first stage No. 1 at the top of the reactor.

This procedure provides for an improvement of the utilization rate of a catalyst before discharge from the reactor. In addition, the fractionation of the reactor in a series of catalyst beds, improves the efficiency of the reactor. The main problem encountered in that type of reactor, concerns the transfer of the catalyst from one stage to the next stage below.

It has first been proposed to allow the catalyst to progressively go down through all the stages, but this has the major disadvantage of mixing, at each stage, a relatively highly active catalyst of stage n with a relatively less active catalyst of stage n+1, which results in a relatively poor use of the catalyst.

It has also been proposed to transfer the catalyst periodically in separated charges or "batches", which obviates partially some of the preceding disadvantages. But any one of these methods requires the use of valves, with or without hydrogen feed to the transfer duct, above the one or more valves. However, the use of such valves, as described for example in U.S. Pat. No. 3,708,420, involves a risk of rapid wear and deterioration of the valve sealing as a result of the possible presence of abrasive catalyst particles on the valve seat. The construction of the reactor with the positioning of the one or more valves inside the reactor poses difficult problems for their control, their maintenance and their replacement when in operation, as a result of the temperature and pressure conditions and of the corrosive action of the reaction medium. The construction of the reactor with the positioning of the one or more valves outside the reactor as indicated in U.S. Pat. No. 3,708,420, makes it necessary to bore holes at regular intervals in the wall of the reactor for the introduction of the valves and such holes are not desirable in the case of reactors operating both at high temperature and under pressure. Moreover, in the case of catalyst transfer through a duct external to the reactor, the charge is no longer in contact with a sufficient amount of catalyst in the main reaction zone, which disturbs the running of the plant. In addition, by-passing a section of the reactor by means of a lateral duct disturbs the pressure distribution and produces siphonages or even discontinues the catalyst fluidization in said section and, in many ways, results in a substantial disturbance of the reactor operation. Finally, the lateral ducts include knees which interfere with the catalyst flow.

SUMMARY OF THE INVENTION

The present process obviates these disadvantages by proposing a technique wherein the catalyst transfer is considerably improved. In this technique the communication between two contiguous stages or the obturation of the passage therebetween are achieved by making use of the kinetic energy of a fraction of the gas and/or liquid. This realization provides for a simple operation free of mechanical displacement. Moreover, the achievement of the reactor wherein the catalyst displacements are limited by partitions, provides a system equivalent to a reactor cascade either of the type with a bubbling bed, or of the type with a semi-stationary bed, but with only one device for introducing the catalyst and for withdrawing the latter, and a single zone for the disengagement of the liquid, gas and catalyst, if such a zone is required.

It is generally preferred to make use of bubbling beds instead of semi-stationary beds. By semi-stationary bed it is meant a catalyst bed subjected to an insufficient gas and liquid upward flow to produce the fluidization of the bed; but these flow rates are however sufficient to displace the catalyst inside the bed. More precisely, the liquid and gas flow rates are then from 50 to 90% of the flow rates required for obtaining the bed fluidization, usually called, in a conventional manner in the art: "bubbling bed" or "ebullated bed." The catalyst is generally used as extrudates, grains or particles. By "ebullated" it is intended to mean a fluidized bed whether it be a gas or a liquid being injected therethrough.

The present process according to the invention consists of passing the liquid phase (liquid charge or solvent for the reactants, according to the case) and a main stream of hydrogen or of a hydrogen-containing gas, upwardly through at least one catalytic reaction zone comprising several stages. In the process each stage contains a catalyst bed which may be either a semi-stationary bed or a bed at least a portion of which is in dispersed state in the liquid charge (ebullated bed), at least one intermediary stage being in permanent communication respectively with the next lower stage and with the preceding upper stage on the one hand through several openings of small section and, on the other hand, through at least one opening of relatively large section. The catalyst passes from one stage to the next through said opening of relatively large section. Furthermore, the process includes injecting at least one fluid selected from hydrogen, a hydrogen-containing gas and a liquid fluid upwardly below said openings of relatively large section at a flow rate and at a velocity sufficient to slow down or impeds the passage of the catalyst from one stage to the next lower stage through said openings of relatively large section. Additionally the injection is periodically discontinued, or reduced below at least one of said openings of said relatively large section, to allow the downward passage of the catalyst through said opening of relatively large section. Preferably all the stages operates as above-described, with however a slight modification concerning the upper stage and the lower stage. The lower stage is in communication with a duct for withdrawing used catalyst, the latter being controllable through a hydrogen or a hydrocarbon diffuser, as in the other stages, through a valve or any other known device. The reaction product and the hydrogenation gas are withdrawn from the top of the reactor. The upper stage is periodically fed with fresh or regenerated active catalyst.

BRIEF DESCRIPTION OF THE DRAWINGS

The invention is illustrated by the accompanying drawings in which:

FIG. 1 is a schematic side view of the catalytic reaction zone apparatus for catalytic conversion of the present invention;

FIG. 2 is a side view of a distribution box associated with the grids in the apparatus of FIG. 1;

FIG. 3 is a bottom view of the distribution box; and

FIG. 4 is a side view of the distribution box of FIG. 3.

DETAILED DISCUSSION OF THE INVENTION

By relatively large opening, it is meant an opening wherethrough the catalyst easily flows from one stage to another, when the injection of hydrogen-containing gas and/or the injection of the liquid phase is discontinued below the concerned opening. The experts may easily determine from the above indications, when upon knowing the size of the catalyst particles, the practical dimensions to be used. Usually, the opening has a cross-sectional area of at least 2 cm$^2$, but preferably at least 5 cm$^2$. The maximum area of the cross-section depends on the reactor section. It is preferable not to exceed 50% of the cross-sectional area of the reactor.

The remainder of the separating zone between the stages is provided with openings of small section as above-described. Preferably these openings are holes wherethrough the liquid and hydrogen flow upwardly but they do not allow passage of the catalyst which flows in the opposite direction. The perforations are accordingly of relatively small size, usually smaller than 1 cm$^2$ cross-sectional area. These perforations may be of various forms such as circular, rectangular or square, in the form of elongate slots, grids, etc. . . . The preferred form is that of grids made of profiled metal bars separated by a space of, for example, from 0.1 to 10 millimeters. The section of the profiled bars may be advantageously triangular or parabolic. During their positioning, the so-achieved partitions are then arranged in the reactor so that the pointed portion is oriented downwardly.

The achievement of the partitions by means of the profiled bars, provides for a good compromise between the opening rate (% of the open surface as compared to the total surface), the rigidity and the small resistance to gases and liquids flow.

The shape of the one or more relatively large openings is either circular, square or rectangular, or has any other form compatible with the nature of the separation zone. The periphery of the opening is advantageously provided with an upper edge whose height is higher than 5 mm and preferably higher than 20 mm.

The separating zones between the stages are horizontal or inclined with respect to a horizontal plane. In the case where the liquid and gas flow rates are insufficient to obtain a so-called "bubbling bed," but sufficient to obtain a semi-stationary bed, it is advantageous that the separating zones be inclined with respect to a horizontal plane by an angle equal to or close to the natural slope angle of the catalyst used.

The liquid which may be injected below a relatively large opening may be the charge itself or the solvent of said charge when it is in a gaseous state, but there can also be injected a fraction of the liquid product from the reaction or a fraction of the solvent withdrawn at any level of the reactor.

The injection of hydrogen or of a hydrogen-containing gas and/or of a fraction of the liquid phase, takes place below each relatively large opening, usually from a distribution box (distribution zone) designed so as to provide for a series of fluid jets at high velocity impeding the normal flow of the catalyst through said opening. As a preferred embodiment, the distributor may use hydrogen or a hydrogen-containing gas.

The distributor or distribution box may comprise an assembly of tubes of appropriate diameter, connected at their lower end to a hydrogen gas distribution box. The hydrogen or hydrogen-containing gas pressure in the box is advantageously from 5 to 400% higher than the operating pressure of the reactor. The diameter of the tubes producing the hydrogen gas jet is preferably from 0.25 to 1 cm. It is more advantageous to inject the gas or liquid at a higher flow rate from the periphery of the distributor than from the center thereof. Preferably in the case of a distributor made of tubes, the diameter of the tubes at the periphery of the box on the first row and, optionally, on the second and third rows is from 2 to 20% higher than the diameter of the tubes of the other rows. The tubes may be arranged in a parallel direction to one another or may be slightly divergent towards the exterior according to the relatively high tendency of the liquid phase to cause bubble trains to coagulate. The geometrical shape of the box is preferably the same as that of the relatively large opening controlled thereby. Its surface area is usually at least 0.75 times the area of said opening; it is preferably from one to ten times or preferably from 1.2 to 4 times that of the opening. The vertical distance between the lower level of the separating surface (excluding the edge) and the upper level of the tubes or of the box is usually from 0.15 to 40 cm (more particularly 1.5 to 10 cm).

The dispersed catalyst may fill the total volume available at each stage (expansion rate of 100%), or only a portion of said volume. Expansion rates from 10 to 70% are preferred. It is known that the expansion rate largely depends on the liquid flow rate. A portion of the catalyst may remain undispersed in the form of a relatively dense layer laying on the plates at each stage and thus forming a fraction of a semi-stationary bed.

The number of openings of relatively large section at each stage is at least 1; it may be greater and, for example, from 2 to 10 openings. The total area of these openings, at a given stage, preferably does not exceed 50% of the cross-sectional area of the reactor.

The catalyst particles usually have an average diameter from 0.12 to 10 mm, these values being however not limitative.

A first type of reaction which can be conducted according to the process of the invention is the removal of pollutant compounds contained in various hydrocarbon cuts.

The hydrocarbon charges so treated according to the invention are then liquid hydrocarbons or hydrocarbon mixtures containing pollutants which may be of various natures.

In a particularly advantageous application, relatively heavy charges may be treated such as, for example, crude oils or distillation residues containing such impurities as sulfur and/or nitrogen compounds, asphalts, metal or organometallic compounds. The involved reactions are those applicable to heavy charges of this type, particularly desulfurization, denitrogenization, hydrocracking, hydrogenation and demetallization.

Another type of reaction is "the hydrogenation" or hydrogen treatment of coal or bituminous shales dissolved or dispersed in a flowing hydrocarbon solvent.

Another type is the hydrogen treatment of used oils to remove therefrom additives and organometallic particles and improve, by hydrogenation, their lubricating power and stability to oxidation and temperature.

The operating conditions of the above-described reactions are usually conducted at a temperature of from 270° to 455° C., a pressure of from 20 to 300 atmospheres, and a hourly flow rate of the liquid charge or solvent of from 0.1 to 15 volumes per volume of catalyst. However, these values are not limitative and depend on the nature of the charge or the degree of severity required in the treatment to be performed.

The catalysts are often of a known type as already used in similar reactions, for example compounds of metals from group VI and/or VIII, used as such or deposited on carriers such as, for example, alumina, silica-alumina, silica, magnesia, bauxite, red-muds, clay, kieselgur, etc. . . . Examples of metal compounds are molybdenum, tungsten, nickel, cobalt and/or iron oxides and preferably sulfides. These catalysts are of conventional type and may be prepared in a known manner.

The process according to the invention and the above-described apparatus are generally used for all catalytic non-catalytic processes where it is desired to achieve counter-current contact with a liquid fluid of a solid divided in particles of a size comparable to that of catalysts.

A particularly significant example is the synthesis of hydrocarbons or alcohols by reacting such gases as CO and $H_2$ in a flowing hydrocarbon liquid phase. Among these hydrocarbon synthesis reactions, there will be described particularly the synthesis of methane or methanation.

For carrying out this reaction, the composition of the synthesis gas mixture expressed by the molar ratio hydrogen/carbon monoxide, is advantageously selected to be from 1/1 to 6/1. Preferably the ratio will be close to 2.5 to 3/1, which corresponds to the theoretical stoichiometry of the reaction. The liquid used as a solvent for the gaseous reactants is, for example, injected at the bottom of the reactor through a duct such as duct 1 in FIG. 1, at a rate, for example, from 1 to 100 liter/liter of catalyst per hour. The gas reactants are injected through another duct, not shown in FIG. 1, and at different levels of the reactor, for example through ducts such as 12, 13 and 15. The liquid solvent must exhibit properties of both chemical inertia and thermal stability. Good results are obtained with saturated hydrocarbons, particularly with paraffinic hydrocarbons in the liquid state under the reaction conditions, for example heptane, octane, dodecane, hexadecane or with mixtures of these hydrocarbons, for example liquid oil or paraffin cuts.

The pressure of the synthesis mixture of hydrogen/carbon monoxide may vary from the atmospheric pressure up to 80 bars or more, but the operating pressure will be preferably from 1 to 20 bars.

The hourly volume flow rate, expressed by the volume of synthesis gas mixture supplied, under normal conditions, per volume of reactor and per hour (VVH) may vary from 1 to 500. Preferably, a VVH of from 50 to 200 are used, which corresponds to a rate of from about 500 to 1000 liter/liter of catalyst/h.

The reaction temperature may be selected from 100 to 450° C. The catalyst is a conventional methanation catalyst and more particularly, a catalyst based on nickel or a nickel compound deposited on a suitable carrier, for example, alumina or kieselguhr.

Among the alcohol synthesis reactions, there will be described particularly the methanol synthesis and the synthesis of higher homologous alcohols.

The liquid solvent, its flow rate (i.e. its space velocity) and the conditions of the injection of the liquid and gaseous fluids are substantially the same as those indicated above for the methanation reaction. In the present case, the gas reactants usually consist either of a mixture $CO + H_2$, or of a mixture $CO_2 + CO + H_2$ (synthesis gas). The operating conditions are well known. The temperature is, for example, from 150° to 350° C., the pressure being from 20 to 200 bars, the molar ratio $H_2/CO$ or the molar ratio $H_2/CO + CO_2$ being from 1.5 to 10, with a volume flow rate from 1,000 to 10,000 $m^3$ (N.T.P.) of gas (mixture $CO + H_2$ or mixture $CO + CO_2 + H_2$) per $m^3$ of catalyst and per hour. As a catalyst, there is used any conventional catalyst, for example based on at least one metal or compound of metal such as copper, cobalt, chromium, iron, vanadium, manganese, rare earth, zinc, alkali metals deposited or not on a carrier such as, for example, alumina.

The liquid charge and optionally also a hydrogen-containing gas are introduced through line 1 (FIG. 1). The mixture flows upwardly in the reactor 2 and passes through the grid 3, then the grid 4 and the grid 5. It issues through line 6.

A cyclone, not shown, provides for the removal of the liquid phase freed from catalyst when the disengagement zone is insufficient to achieve a perfect separation of the catalyst, the liquid and the gas. The equipment thus comprises, according to this figure, 4 stages 7, 8, 9 and 10. Fresh catalyst is introduced through line 11 and hydrogen or a hydrogen-containing gas through lines 12, 13, 14 and 15 feeding the distribution boxes 16, 17, 18 and 19. The grids 3, 4 and 5 are provided with so-called relatively large openings 20, 21, 22 and 23, centered above the distributors and provided with edges such as 26 (see FIG. 2). More and more used catalyst, for example, in the case of purification of heavy hydrocarbon charges, is present in stages 9, 8 and 7 respectively. The flow rate of liquid and gas and the diameter of the reactor are so selected as to maintain the catalyst in a dispersed or expanded state in stages 9 and 10 and at least partially in a semi-stationary state in stages 7 and 8.

This difference in the hydrodynamic state between the 4 stages results from the fact that, in the lower stages 7 and 8, the catalyst, whose composition is given in the following examples, becomes heavy, in the case of, for example, the purification of heavy hydrocarbon charges, with metals, mainly nickel and vanadium, and with coke, and accordingly, its density becomes higher than that of the fresh catalyst of the upper stage (No. 10) and of the substantially unpolluted catalyst of the next lower stage (No. 9). Moreover, the hydrogen injection through such injectors as 16, 17, 18, increases the gas velocity in the upper portion of the reactor and facilitates the transition to the "bubbling bed" state in the upper stages.

The catalyst does not flow from one stage to the other as a result of the kinetic energy of the hydrogen gas jets supplied by the distributors 16, 17, 18 and 19 and passing through the openings 20, 21, 22 and 23.

After a certain period of use, without interrupting the hydrocarbon and hydrogen flow introduced through line 1, the valve 25 on line 24 is opened for withdrawing the catalyst. When a portion or preferably the totality of the catalyst has left stage 7, the hydrogen or hydrogen-containing gas injection through line 12 is discontinued: the catalyst thus passes from stage 8 to stage 7 through the opening 20. Hydrogen is again injected through line 12 and the hydrogen feed is discontinued through line 13 and 14 to allow the catalyst to flow down from stage 9 to stage 8. The procedure is similar for the upper stages 9 and 10.

It is also possible to discontinue the injection of hydrogen (or of a hydrogen-containing gas) simultaneously through lines 12, 13, 14 and 15: thus, the catalyst flows down from one stage to the next, but at each stage, a catalyst mixing occurs to a certain extent and preferably this must be avoided.

The design of the apparatus is exactly the same in the case of a liquid stream used instead of hydrogen or of a hydrogen-containing gas and flowing through pipes 12, 13, 14 and 15 for impeding the catalyst flow through openings 20, 21, 22 and 23.

FIGS. 2 through 4 show, in detail, portions of the apparatus. Particularly, FIG. 3 is a view from below of the distribution box; a side view of the same box is shown in FIG. 4.

The FIGS. 2, 3 and 4 show the position of tubes such as 27 and 28 in a distribution box of rectangular shape 16 corresponding to a rectangular opening 20 (in FIG. 2), in a grid 3 (in FIG. 2) formed of profiled metal bars of triangular section; 26 (in FIG. 2) designates the edge of the opening, 28 (in FIGS. 3 and 4) shows one of the tubes located at the external periphery of the box; these tubes have a diameter slightly larger than that of the other tubes such as 27 (on FIG. 3) located further toward the interior. Pipe 29 of FIGS. 2, 3 and 4 is used for feeding the distribution box either from a high pressure pipe 30 internal to reactor 2 (see FIG. 2), or through a passage-way through the reactor wall.

In other cases, the distribution box may be simply constructed from a box having a perforated face, or provided with a fritted surface, or with any other means for obtaining fluid jets of high velocity.

The present process may also be performed in several reactors, with having dispersed catalyst and/or a semi-stationary bed of the type described, these reactors being optionally associated in series or in parallel. It is also possible to provide one or more stationary bed reactors, following one or more reactors with dispersed or semi-stationary catalysts beds of the described type, these stationary bed reactors being optionally used to complete the reaction or to proceed to a different reaction, for example saturating hydrogenation, hydrodesulfidation, hydrodenitrogenization, hydrocracking, catalytic cracking, hydrorefining or hydrofinishing.

EXAMPLE 1

By way of example, to clarify the performance obtained by the reactor of the invention, the treatment was performed on a straight run residue of heavy Iran type, whose properties are mentioned in Table I, in three different tests, all involving the same amount of catalyst and the same flow rate of fresh hydrocarbon.

The catalyst used in the three series of tests is of the cobalt-molybdenum alumina type. It is presulfided before being introduced into the reactors used in the 3 tests. Its total pore volume is 0.50 cc/g, it contains by weight, 3% of cobalt oxide and 14% of molybdenum oxide. It is in the form of extrudates of a 1.4 mm diameter and an average length of 8 mm.

The first test which will be called "Case A" concerns the use of the catalyst in a single stage bubbling bed, not in conformity with invention.

The second test, which will be called "Case B" provides for the use of a catalyst in a reactor according to the invention comprising 4 stages of substantially the same volume. Hydrocarbon withdrawals at the level of each bed indicates the advance rate of the reaction and the accumulation of vanadium onto the catalyst. The results are reported in Table II. The stages are indicated with reference numbers 1, 2, 3 and 4, while following the upward flow of the hydrocarbons. The catalysts flows downwardly.

The reactor used in each of the two test ("Case A" and "Case B") has a ratio $H/D=13$ (height/diameter). The total pressure is 90 bars at the reactor outlet. In "Case A" the flow rate of the hydrogen gas is 1480 liters NTP of gas per liter of charge at 15° C. The total amount of the gas is injected at the bottom of the reactor, in admixture with the charge. In "Case B", 1000 liters of hydrogen gas per liter of charge are injected at the bottom of the reactor and, in addition, 120 liters of hydrogen per liter of charge are injected between each stage, through diffusers or distribution boxes. From the above-defined hydrodynamic conditions, it is clear that the bed is a semi-stationary bed in the lower stages 1 and 2 and an ebullated bed in the upper stages 3 and 4. In the two tests ("Case A" and "Case B"), the average temperature is 390° C.

In "Case B", the reactor includes the additional following features:

Two so-called "large" openings in each partition between two stages, cross-sectional area of each opening: 15 cm$^2$; shape of the opening: rectangular.

Diameter of the so-called small section openings: about 0.3 cm$^3$ in the form of grids made from profiled metal bars spaced at a distance of about 4 mm.

Height of the edges 26 of FIG. 2: 25 mm.

Distribution box similar to that of FIGS. 4 and 5; diameter of the tubes located above the periphery of the distribution box: 0.5 mm; diameter of the other tubes: 0.45 mm; cross-sectional area of each distribution box equal to about 2 times the surface of the so-called "large" opening controlled therefrom.

Average vertical distance between the lower level of the separating surface (excluding the edge) and the upper level of the tubes: 20 cm.

In the third test, the same catalyst amount as the two other tests is used in a stationary bed, in a conventional down flow operated reactor having a height to diameter

TABLE II

| OBTAINED PRODUCTS | | CASE A 1 SINGLE STAGE | CASE B 1st STAGE | CASE B 2nd STAGE | CASE B 3rd STAGE | CASE B 4th STAGE |
|---|---|---|---|---|---|---|
| Properties of the 180° C.+ cut | | | | | | |
| Density | g/cc | 0.95 | | | | 0.920 |
| Sulfur | % b.w. | 0.93 | 1.83 | 0.75 | 0.54 | 0.47 |
| Nitrogen | ppm | 3570 | | | | 3192 |
| Conradson carbon | % b.w. | 7.0 | | | | 5.8 |
| Vanadium | ppm | 101 | 135 | 91 | 73 | 66 |
| Vanadium on the catalyst in % of new catalyst | | 16.6 | 22.2 | 11.5* | 4.1* | 1.2* |
| Temperature | °C. | 390 | 405 | 405 | 388 | 365 |
| Average temperature | °C. | 390 | | 390°C. | | |
| Total performances | | | | | | |
| Hydrodesulfidation | % b.w. | 64.2 | | 81.9 | | |
| Hydrodenitrogenization | % b.w. | 15 | | 24 | | |
| Vanadium removal | % b.w. | 49.5 | | 67 | | |
| Ratio of added catalyst to the fresh charge mass | % b.w. | 0.6 kg/t | | 0.6 kg/t | | |
| Ratio of the hourly flow rate of the fresh charge by weight to the catalyst weight | | 0.83* | | 0.83 h$^{-1}$ | | |

*Calculated from hydrocarbon analyses.

ratio of H/D=4. The gas and liquid flow rates and the pressures are the same as those used for the first two tests. The average temperature of the reactor is 370° C., corresponding to the catalyst and the charge to a normal temperature of the cycle beginning. The characteristics of the obtained products are reported in Table III.

From the observation of the discharged catalysts and of the products obtained, it is apparent that the staged reactor according to the invention ("Case B") is much more efficient than a single stage reactor as that of "Case A". It provides for a better use of the catalyst issuing from the reactor with a higher methane content for the same rate of addition of new catalyst.

Moreover, the comparison of Table II ("Case B") and Table III shows that in the reactor according to the invention, there is obtained, at an average temperature of 390° C., the removal of sulfur, nitrogen and metals and a reduction of Conradson carbon similar to those obtained in a conventional reactor with a stationary bed, at 370° C., at the beginning of the cycle, the other conditions being substantially unchanged. However, in the case of a stationary bed catalyst, the metals (Ni and V) deposited on the catalyst will progressively deactivate said catalyst, and it is consequently necessary to progressively increase the average temperature of the reactor. After about 1200 hours, the catalyst contains about 20% of (Ni+V) and it is necessary to stop the operation of the plant, to discharge the used catalyst and to replace it with a new charge of catalyst. The reactor, designed in accordance with the invention, has the advantage of being kept in operation, due to the possibilities of introducing new catalyst and of withdrawing used catalyst.

TABLE I

| CHARACTERISTICS OF THE STRAIGHT RUN RESIDUE OF "HEAVY IRANIAN" TYPE. | | |
|---|---|---|
| Cut | 350° C.+ | |
| Density (d) | 0.970 | g/cm$^3$ |
| Sulfur (S) | 2.6 | % by weight |
| Nitrogen (N) | 4200 | ppm (part per million) |
| Conradson carbon | 10.7 | % by weight |
| Asphaltens | 4.15 | % by weight |
| Nickel | 75 | ppm |
| Vanadium | 200 | ppm |

TABLE III

| Third test | | |
|---|---|---|
| Fixed bed reactor | | |
| Properties of the produced 180° C.+ cut | | |
| Density | 0.940 | g/cm$^3$ |
| Sulfur | 0.44 | % b.w. |
| Nitrogen | 3150 | ppm |
| Conradson carbon | 5.6 | % b.w. |
| Vanadium | 56 | ppm |
| Hydrodesulfidation | 83 | % b.w. |
| Hydrodenitrogenization | 25 | % b.w |
| Vanadium removal of the cycle beginning | 72 | % b.w. |
| Average temperature of the reactor | 370° C. | |
| Ratio:hourly flow rate by weight of fresh charge/catalyst weight | 0.83 h$^{-1}$ | |

EXAMPLE 2

This example relates to the manufacture of methane from hydrogen and carbon monoxide. As liquid solvent there is used a hydrocarbon cut of naphthenic and paraffinic type whose boiling point is in the range from 350° to 450° C. The average temperature for performing the reaction is 340° C. The solvent temperature at the inlet of the reactor is 320° C.; the solvent temperature at the outlet of the reactor is 350° C. The average temperature of the gas-solvent mixture is 300° C. The operation is conducted under a pressure of 40 bars. The volume velocity of the solvent is 20 1/1 catalyst/hour and the volume velocity of the gas (CO+H$_2$) is 3,000 1/1 catalyst/hour. There is used a catalyst consisting of nickel deposited on kieselguhr (50% by weight of nickel) as extrudates of a 2 mm diameter and a 5 mm length. The ratio H$_2$/CO is 2.5.

In test called "Case A$_1$" the catalyst is used as a "bubbling bed" in a single stage, not in conformity with the invention.

In a second test which will be called "Case $B_1$", the catalyst is used in a reactor according to the invention comprising 4 stages substantially of the same volumes (same characteristics as the "Case B" reactor of Example 1). The reactor used in each of these two test (Case $A_1$ and Case $B_1$) has a ratio of H/D=13 (height/diameter). In test "Case $A_1$", the total amount of the gas is injected at the bottom of the reactor. In the test "Case $B_1$" there is injected, on the one hand, 2,700 liters of gas per liter of catalyst per hour and 300 liters of gas per liter of catalyst and per hour through the diffusers or distribution boxes. In each of the 4 stages, the catalyst is in a "ebullated bed".

In the two tests, the solvent withdrawn from the top of the reactor passes through an exchanger, which lowers its temperature to 300° C., and then reaches a separator, surmounted with a cooler whereby the temperature of the reaction gas is decreased to about 40° C.

In "Case $A_1$", there is obtained, at the top outlet of the reactor a gas whose composition by volume is as follows (expressed as dry gas):

| | |
|---|---|
| Methane | 85% |
| Ethane | 6% |
| CO | 2% |
| $CO_2$ | 3.5% |
| $H_2$ | 3.5% |

In "Case $B_1$", there is obtained, at the top outlet of the reactor, a gas whose composition by volume is as follows (expressed as dry gas):

| | |
|---|---|
| Methane | 90% |
| Ethane | 3% |
| CO | 1% |
| $CO_2$ | 3% |
| $H_2$ | 3% |

EXAMPLE 3

This example concerns the manufacture of methanol from hydrogen and carbon monoxide. The liquid solvent is the same as in example 2. The average temperature of the reaction is 230° C. The temperature of the solvent at the inlet of the reactor is 220° C.; the temperature of the solvent at the outlet of the reactor is 240° C. The average temperature of the gas-solvent mixture is 200° C.

The operating pressure is 100 bars. The space velocity of the solvent is 15 1/1. catalyst/hour and the space velocity of the gas ($CO+H_2$) is 6,000 1/1. catalyst/hour. The catalyst consists of balls of a diameter from 2.5 to 3.5 mm, said catalyst containing by weight:

40% of CuO
20% of ZnO
10% of alumina
30% of secar cement, used as binder.

In a test called "Case $A_2$", the catalyst is used in a bubbling bed of a single stage, not in conformity with the invention.

In a second test, which will be called "Case $B_2$", the catalyst is used in a reactor according to the invention comprising 4 stages of substantially the same volume (same characteristics of the reactor as in "Case B" of Example 1). The reactor in these two tests (Case $A_2$ and Case $B_2$) has a ratio of its height to its diameter: H/D=13. In test "Case $A_2$", the totality of the gas is injected at the bottom of the reactor. In test "Case $B_2$" there is injected on the one hand 5,400 liters of gas per liter of catalyst per hour and 600 liters of gas per liter of catalyst and per hour through the diffuser or distribution boxes. The catalyst is present as a ebullated bed in each of the 4 stages.

In the two tests, the volume withdrawn from the top of the reactor passes through an exchanger which decreases its temperature to about 200° C. and then reaches a separator overtopped with a cooler whereby the temperature of the reaction gas can be decreased to about 30° C.

In the test "Case $A_2$", the conversion rate of CO is 47% and there is obtained a mixture containing by weight 99% of methanol and 1% of higher homologous alcohols (ethanol, n-propanol, isopropanol, n-butanol and isobutanol). In test "Case $B_2$", the conversion rate of CO is 50% and there is obtained a mixture also containing by weight 99% of methanol and 1% of higher homologous alcohols.

What is claimed is:

1. A liquid phase process for the catalytic conversion of hydrocarbons or carbon monoxide in the presence of hydrogen, consisting essentially of passing a liquid phase and a hydrogen-containing main gas stream upwardly through at least one catalytic reaction zone comprising several superposed stages, the at least one catalytic reaction zone containing a catalyst bed in each stage which may be either a semi-stationary bed or an ebullated bed, at least one intermediary stage being in permanent communication respectively with the next lower stage and with the preceding upper stage, through a perforated support having multiple openings having small cross-sections of a size smaller than the catalyst particles, and through respective at least one opening having large cross-sections substantially larger than the catalyst particles, the large cross-section openings adapted to allow periodical passage of the catalyst from one stage to another, the process comprising periodically injecting at least one fluid selected from hydrogen, a hydrogen-containing gas and a liquid hydrocarbon, upwardly, from below said openings of relatively large cross-section, at a flow rate and a velocity sufficient to substantially slow down or impede the passage of the catalyst from one stage to the next lower stage through said openings of relatively large cross-section, and periodically discontinuing the injection, or periodically reducing the injection flow rate from below at least one of said openings of relatively large cross-section, to allow passage of the catalyst, downwardly through said at least one of said openings of relatively large cross-section from one stage to the next lower stage.

2. A process according to claim 1, wherein all said intermediary stages operate as indicated in claim 1, and further comprising periodically feeding fresh catalyst into the upper stage, and at least a portion of the used catalyst present in the lower stage being periodically discharged therefrom.

3. A process according to claim 2, wherein each opening having a relatively large cross-section has a cross-sectional area of at least 2 $cm^2$, the total area of the cross-sections being no greater than 50% of the total cross-sectional area of the reaction zone.

4. A process according to claim 3, wherein said openings of small cross-section as defined in claim 1, each have a cross-sectional area of less than 1 $cm^2$.

5. A process according to claim 4, wherein said injection of the fluid selected from hydrogen, a hydrogen-containing gas and a liquid hydrocarbon, is performed from a distribution zone located from 0.15 to 40 cm below each of the relatively large cross-section area openings, the area of said distribution zone being equal to at least 0.75 times the area of the relatively large opening associated therewith, the liquid hydrocarbon being selected from at least a portion of the initial charge, or of the reaction product, or of an intermediary effluent of the charge subjected to said catalytic process.

6. A process according to claim 5, wherein said fluid is injected under a feeding pressure from 5 to 400% higher than the operating pressure of the reaction zone.

7. A process according to claim 1, wherein the catalyst is in an "ebullated" state at each stage.

8. The use of the process according to claim 1, for the hydrotreatment of hydrocarbons or bituminous shales.

9. A process as in claim 1 wherein said injection flow is reduced for a sufficient period of time for allowing substantially all of the catalyst in an upper stage to move to the next lower stage.

10. In a liquid phase process for the catalytic conversion of hydrocarbons or carbon monoxide in the presence of hydrogen, comprising the passing of a liquid phase and a hydrogen containing main gas stream upwardly through at least one catalytic reaction zone comprised of several superposed stages, each stage containing a catalyst bed of either a semi-stationary bed type or an ebullated bed type, at least one intermediate stage being in permanent communication respectively with both the next lower stage and with the preceding upper stage through: (a) a perforated support having multiple openings having small cross sectional areas of a size smaller than the catalyst particles, and (b) through at least one opening of large cross-section substantially larger than the catalyst particles, the improvement comprising the steps of:

periodically injecting at least one fluid selected from a hydrogen-containing gas and a liquid hydrocarbon, upwardly through said at least one opening of large cross-section, at a flow rate sufficient to substantially impede the passage of catalyst from each upper stage to the next lower stage through said at least one opening of large cross-section; and periodically reducing the injection flow rate of said at least one fluid sufficient to allow passage of the catalyst through said at least one opening of large cross-section, whereby substantially only relatively less active catalyst is removed from the catalytic reaction zone while maintaining relatively more active catalyst therein.

* * * * *